United States Patent
Bünger et al.

(10) Patent No.: US 6,660,251 B1
(45) Date of Patent: Dec. 9, 2003

(54) GALENIC FORMULATION CONTAINING BIOTIN

(75) Inventors: Joachim Bünger, Gross-Umstadt-Heubach (DE); Hansjürgen Driller, Gross-Umstadt (DE); Wolfgang Wohlrab, Halle (DE); Lothar Motitschke, Hilden (DE); Christoph Huschka, Halle (DE); Reinhard Neubert, Halle (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/890,294

(22) PCT Filed: Jan. 14, 2000

(86) PCT No.: PCT/EP00/00248

§ 371 (c)(1),
(2), (4) Date: Jul. 27, 2001

(87) PCT Pub. No.: WO00/44342

PCT Pub. Date: Aug. 3, 2000

(30) Foreign Application Priority Data

Jan. 28, 1999 (DE) .......................... 199 03 241

(51) Int. Cl.⁷ ............................. A61K 6/00; A61K 7/00; A61K 7/04
(52) U.S. Cl. ......................................... 424/61; 424/401
(58) Field of Search ................................ 424/400, 401, 424/59, 64, 70.7

(56) References Cited

U.S. PATENT DOCUMENTS

| 5,166,168 A | * | 11/1992 | Stiefel .................... 514/387 |
| 5,710,177 A | * | 1/1998 | Sauermann et al. ........ 514/557 |
| 5,785,959 A |  | 7/1998 | Wolf et al. |
| 5,925,366 A |  | 7/1999 | Wolf et al. |

FOREIGN PATENT DOCUMENTS

| DE | 19615576 A1 |  | 10/1997 |
| EP | 0 222 664 | * | 5/1987 |

OTHER PUBLICATIONS

Williams A C et al: "Urea Analogues in Propylene Glycol as Penetration Enhancers in Human Skin" International Journal of Pharmaceutics, vol. 56, No. 1, Nov. 1, 1989.

\* cited by examiner

*Primary Examiner*—Thurman K. Page
*Assistant Examiner*—S. Howard
(74) *Attorney, Agent, or Firm*—Millen, White, Zelano & Branigan, P.C.

(57) ABSTRACT

The invention relates to galenic formulations which contain a) one or more compounds selected from biotin, its physiologically compatible salts, biotin esters and the stereoisomeric forms of these compounds; and b) one or more compounds selected from urea and urea derivatives. The above formulations are suitable for use as topically administered formulations for the cosmetic and/or medical treatment of the skin, hair and/or nails.

16 Claims, 4 Drawing Sheets

GALENIC FORMULATION CONTAINING BIOTIN

The invention relates to topically applicable galenic formulations which contain one or more compounds selected from biotin, the physiologically tolerable salts of biotin, biotin esters and the stereoisomeric forms of these compounds and one or more compounds selected from urea and urea derivatives and are suitable for the cosmetic or medicinal treatment of skin, hair and/or nails, for example for the treatment of diseases or functional disorders of human or animal skin, hair and/or nails.

The chemical name for biotin is hexahydro-2-oxiothieno[3,4-d]imidazole-4-valeric acid. Its chemical structure corresponds to the formula The efficacy of biotin in skin, hair and nail diseases has been assessed in different ways in the past. Although, by means of continuous biotin therapy, it was possible to show the efficacy in the case of soft, brittle and splitting nails, different forms of alopecia and atopic and seborrheic dermatitis in a detectable manner, use remained sparing, as this is associated, despite no side effects at all, with the necessity of an extended treatment period of several months (R. Bitsch et al. (1994) Biotin, Wissenschaftliche Verlagsgesellschaft mbH, Stuttgart; V. E. Colombo et al. (1990) Treatment of brittle fingernails and onychoschizia with biotin: scanning electron microscopy. J. Am. Acad. Dermatol. 23: 1127–1132; G. L. Floersheim (1989) Behandlung brüchiger Fingernägel mit Biotin [Treatment of brittle fingernails with biotin]. Z. Hautkr. 64: 41–48; G. L. Floersheim (1992) Prüfung der Wirkung von Biotin auf Haarausfall und Haarqualität [Testing the action of biotin on hair loss and hair quality]. Z. Hautkr. 67: 246–255; W. Gehring (1996) Der Einfluss von Biotin bei reduzierter Nagelqualität. Eine plazebokontrollierte doppelblinde klinische Studie [The influence of biotin on reduced nail quality. A placebo-controlled double-blind clinical study]. Akt. Dermatol. 22: 20–25; U. Siebert et al. (1996) Zur Dosierung und Wirkung von Biotin bei Nagel- und Haarwachstumsstörungen [The dosage and action of biotin in nail and hair growth disorders]. Zeitschrift Hautnah 6: 438–443).

It is known that topically applied biotin-containing formulations having a biotin content of 0.25% and 0.50% lead to a visible reduction in the development of wrinkles on the skin of old people (L. Gilli et al. (1995) Beeinflussung der Fältchenausprägung bei Altershaut durch topisch appliziertes Biotin [Influencing the development of wrinkles on the skin of old people by means of topically applied biotin]. Z. Hautkr. 70 (6): 419–425). In these investigations, it was not possible to show any epithelial and histopathological changes at all in the areas treated.

Regardless of the positive clinical experience with biotin, knowledge about the mechanism of action is incomplete. From the present state of knowledge, biotin, as a coenzyme, has a number of carboxylases which are linked in with various vital metabolic functions (R. Bitsch et al. (1994) Biotin. Wissenschaftliche Verlagsgesellschaft mbH, Stuttgart). In addition to its function as a coenzyme, the independent pharmacological effects of biotin, e.g. the influence on the keratin structure, are of interest for therapeutic use. The underlying mechanism of the influence on the growth and differentiation behavior of the keratinocytes, however, is controversial (A. Fritsche (1990) Biotin verändert das Zytokeratinmuster von kultivierten Keratinozyten [Biotin changes the cytokeratin pattern of cultured keratinocytes], inaugural dissertation, University of Zurich; A. Fritsche et al. (1991) Pharmakologische Wirkungen von Biotin auf Epidermiszellen [Pharmacological effects of biotin on epidermal cells]. Schweiz. Arch. Tierheilk. 133: 277–283; A. Limat et al. (1996) Proliferation and differentiation of cultured human follicular keratinocytes are not influenced by biotin. Arch. Dermatol. Res. 288: 31–38).

Owing to its hydrophilic properties, biotin belongs to the substances for which the horny layer, with its lipophilicity and the low hydration in the normal state, represents a penetration barrier of particular size.

For the topic application of biotin there thus exist particular galenic requirements.

The object was thus to make available topically applicable galenic formulations which contain compounds selected from biotin, the physiologically tolerable salts of biotin, biotin esters and the stereoisomeric forms of these compounds and are suitable for the cosmetic or medicinal treatment of skin, hair and/or nails.

Surprisingly, it has now been found that this object is achieved by the provision of galenic formulations comprising a) one or more compounds selected from biotin, the physiologically tolerable salts of biotin, biotin esters and the stereoisomeric forms of these compounds and b) one or more compounds selected from urea and urea derivatives.

The invention furthermore relates to the use of one or more compounds selected from biotin, the physiologically tolerable salts of biotin, biotin esters and the stereoisomeric forms of these compounds and of one or more compounds selected from urea and urea derivatives for the production of a topically applicable galenic formulation, a process for the production of a topically applicable galenic formulation, characterized in that one or more compounds selected from biotin, the physiologically tolerable salts of biotin, biotin esters and the stereoisomeric forms of these compounds and one or more compounds selected from urea and urea derivatives are brought into a suitable formulation form, if appropriate with further active compounds, excipients and/or vehicles.

The application of the galenic formulations according to the invention can take place both to humans and to animals. The galenic formulations according to the invention can be used both in cosmetics and in human and in veterinary medicine. The areas of use of the galenic formulations according to the invention relate to the therapy, prophylaxis and/or metaphylaxis of skin diseases, of functional disorders of the skin, of skin-ageing processes and of dry skin conditions.

The invention furthermore relates to the use of a) one or more compounds selected from biotin, the physiologically tolerable salts of biotin, biotin esters and the stereoisomeric forms of these compounds and b) one or more compounds selected from urea and urea derivatives for the production of a topically applicable galenic formulation for improving the penetration of the compounds selected from biotin, the physiologically acceptable salts of biotin, biotin esters and the stereoisomeric forms of these compounds into deeper layers of human or animal skin, mucous membrane and/or nails, for the protection, for the maintenance and/or for the reconstruction of the normal function and structure of human or animal skin and/or for the prevention of environmentally related skin damage, for example UV-related skin damage, for the treatment of diseases of the hair, sebaceous and/or sweat glands of human or animal skin and/or for cosmetic skin treatment, in particular for skin care.

In particular, "penetration of biotin into deeper layers of human skin", for example, in the context of the present invention means that biotin penetrates through the horny layer of the human skin. Without a penetration enhancer, biotin does not penetrate or does not penetrate in an efficacious concentration through the horny layer of the human skin. However, it has been found, for example, that the penetration of topically applied biotin through the horny layer into human skin is improved if biotin is combined with a penetration enhancer, preferably with urea and particularly preferably with urea in an emulsion. It has been found that the combination of biotin with a penetration enhancer of this type makes possible, for example, the penetration of biotin into the living epidermis in an efficacious concentration.

In the context of the present invention, penetration enhancers are designated as substances which, for example, increase the permeability or increase the penetration of the active compounds at the site of application.

The application of the galenic formulations according to the invention make possible, for example, the penetration of biotin in adequate concentration of at least $10^{-5}$ mol/l for the treatment of diseases of the hair, sebaceous and/or sweat glands of the skin. The use of the galenic formulations according to the invention on finger- and/or toenails makes possible, for example, the penetration of biotin in a concentration of at least $10^{-5}$ mol/l into the deep portions of the nail and/or the nail matrix. Customarily, approximately 10 min to 24 h, for example, after topical application of the galenic formulation according to the invention to the prickle-cell layer and/or to the basal-cell layer of the skin a biotin concentration is achieved which is suitable for the stimulation of epidermal lipid synthesis and is at least $10^{-5}$ mol/l.

Moreover, it has been found that the influence of biotin on lipid synthesis is concentration-dependent. This result is shown in FIGS. 1 to 4.

While low biotin concentrations in the medium ($10^{-6}$ mol/l) can be classified as inefficacious, the lipid synthesis power of keratinocytes could be increased at higher biotin concentrations in the medium ($10^{-5}$ to $10^{-3}$ mol/l).

Increases in the concentration of the fatty acids myristic acid (MA), palmitic acid (PA), stearic acid (SA) and oleic acid (OA) under the action of biotin were detected both in the culture of HaCaT keratinocytes, and in native human keratinocytes. The absence of an increase in the concentration of linoleic acid (LA) is to be considered in connection with the inability of the keratinocytes to synthesize polyunsaturated fatty acids independently. The results are shown in FIGS. 1 to 4 for the action of biotin on human cultured HaCaT keratinocytes.

It has furthermore been found that the penetration of biotin into the human skin is vehicle-dependent, the penetration from the W/O vehicles being markedly lower than the penetration from the more hydrophilic O/W vehicles. However, neither standard W/O nor standard O/W vehicles which do not contain any penetration enhancer are suitable for attaining sufficiently high (epidermal biotin concentrations for stimulation of lipid synthesis. The inadequate penetration of biotin from a standard O/W vehicle which contains no penetration enhancer is shown for the horny layer in FIG. 5 and the epidermis in FIG. 6 (see values for ST O/W in FIGS. 5 and 6).

Vehicle optimization was achieved according to the invention by the addition of urea to the standard vehicle. By means of the incorporation of urea into the standard vehicle, formulations according to the invention result which bring about increased penetration of biotin into human skin. The penetration increase is dependent on the extent of the vehicle used.

For example, the use of an O/W emulsion with 10% urea according to the invention leads, even after a short duration of action of 30 min, to an effective epidermal biotin concentration. The effect was also detectable after a prolonged application period of 300 min. These results are likewise shown in FIGS. 5 and 6 (see values for U O/W in FIGS. 5 and 6).

Figure 7:
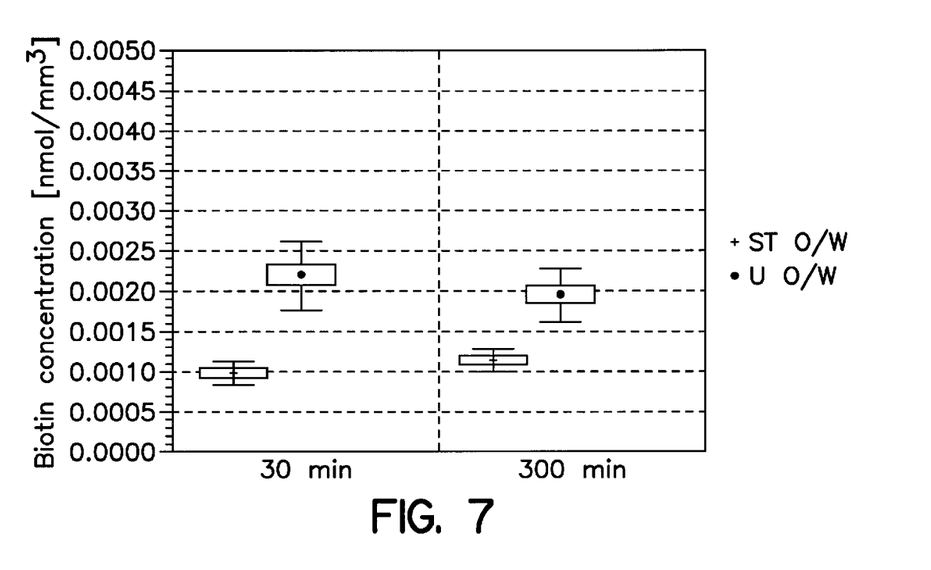

The comparison of the biotin concentration in the dermis after penetration of biotin from a standard O/W vehicle (see values for ST O/W) and after penetration of biotin from a corresponding 10% by weight vehicle comprising urea (see values for U O/W) into human skin ex vivo is shown in FIG. 7.

The biotin concentration in the dermis after penetration of biotin from the vehicle comprising 10% by weight of urea into human skin ex vivo is markedly below 0.01 nmol/mm$^3$ both after 30 min and after 300 min. The concentration of 0.01 nmol/mm$^3$ corresponds to the effective biotin concentration of $10^{-5}$ mol/l from FIG. 2. This shows that owing to the topical application of formulations according to the invention which contain urea, the penetration of biotin through the horny layer can be advantageously controlled in such a manner that the efficacious biotin concentration in the epidermis is exceeded, but remains deficient in the dermis (see FIGS. 6 and 7).

In U.S. Pat. No. 5,166,168, topically applicable formulations are described which contain biotin or a pharmaceutically acceptable salt of biotin and are suitable for the treatment of nail diseases. These formulations can contain penetration enhancers in an effective amount, for example, menthol, propylene glycol, dimethyl sulfoxide, dimethylacetamide, dimethylformamide and azone. However, there is no information on urea or urea derivatives as penetration enhancers.

The compounds selected from biotin, the physiologically tolerable salts of biotin, biotin esters and the stereoisomeric forms of these compounds can be present in the galenic preparations, for example, as optical isomers, diastereomers or racemates.

The biotin esters are characterized by the following generic structural formula:

According to the invention, R is a branched or unbranched alkyl group having 1 to 18 C atoms or a branched or unbranched alkenyl groups having 1 to 18 C atoms. Preferred biotin esters are those in which R is methyl or ethyl.

Among the compounds selected from biotin, the physiologically tolerable salts of biotin, biotin esters and the stereoisomeric forms of these compounds, biotin is preferred, in particular D-cis-hexahydro-2-oxothieno [3,4] d]imidazole-4-valeric acid of the formula Biotin can be used in the formulations according to the invention in the form of any known pharmaceutically acceptable salt. Preferred physiologically tolerable salts of biotin are, for example, alkali metal, alkaline earth metal or ammonium salts, such as Na, K, Mg or Ca salts, and also salts derived from organic bases such as ethylamine, triethylamine, ethanolamine, diethylaminoethanol, ethylenediamine, piperidine, morpholine, 2-piperidinoethanol, benzylamine and procaine.

Suitable urea derivatives, for example, are those which release urea after cleavage. Allantoin is preferred among the urea derivatives.

Urea is preferred among the compounds selected from urea and the urea derivatives.

Among the galenic formulations according to the invention, those which contain biotin and/or urea are thus preferred.

The compounds selected from urea and urea derivatives can be incorporated in different galenic formulations, such as in O/W or W/O emulsions. Urea is preferably incorporated in O/W emulsions.

The galenic formulation is prepared by bringing one or more compounds selected from biotin, the physiologically tolerable salts of biotin, biotin esters and the stereoisomeric forms of these compounds and one or more compounds selected from urea and urea derivatives into a suitable formulation form, if appropriate with excipients and/or vehicles. The excipients and vehicles originate from the group of carriers, preservatives and other customary excipients.

The galenic formulations based on one or more compounds selected from biotin, the physiologically tolerable salts of biotin, biotin esters and the stereoisomeric forms of these compounds and one or more compounds selected from urea and urea derivatives are used externally.

Use forms which may be mentioned are, for example: solutions, suspensions, emulsions, pastes, ointments, gels, creams, lotions, lakes, powders, soaps, surfactant-containing cleansing preparations, oils and sprays. In addition to one or more compounds selected from biotin, the physiologically tolerable salts of biotin, biotin esters and the stereoisomeric forms of these compounds and one or more compounds selected from urea and urea derivatives, any desired customary vehicles, excipients and, if appropriate, further additive compounds are added to the formulation.

The excipients and active compounds optionally contained in the galenic formulations according to the invention can be either of hydrophilic or lipophilic nature.

Preferred excipients are derived from the group consisting of the preservatives, antioxidants, stabilizers, solubilizers, vitamins, colorants and odor enhancers.

Ointments, pastes, creams and gels, in addition to one or more compounds selected from biotin, the physiologically tolerable salts of biotin, biotin esters and the stereoisomeric forms of these compounds and one or more compounds selected from urea and urea derivatives, can contain the customary vehicles, e.g. animal and vegetable fats, waxes, paraffins, starch, tragacanth, cellulose derivatives, polyethylene glycols, silicones, bentonites, silicic acid, talc and zinc oxide or mixtures of these substances.

Powders and sprays, in addition to one or more compounds selected from biotin, the physiologically tolerable salts of biotin, biotin esters and the stereoisomeric forms of these compounds and one or more compounds selected from urea and urea derivatives, can contain the customary vehicles, e.g. lactose, talc, silicic acid, aluminum hydroxide, calcium silicate and polyamide powder or mixtures of these substances. Sprays can additionally contain the customary propellants, e.g. chlorofluorohydrocarbons, propane/butane or dimethyl ether.

Solutions and emulsions, in addition to one or more compounds selected from biotin, the physiologically tolerable salts of biotin, biotin esters and the stereoisomeric forms of these compounds and one or more compounds selected from urea and urea derivatives, can contain the customary vehicles such as solvents, solubilizers and emulsifiers, e.g. water, ethanol, isopropanol, ethyl carbonate, ethyl acetate, benzyl alcohol, benzyl benzoate, propylene glycol, 1,3-butyl glycol, oils, in particular cottonseed oil, peanut oil, maize germ oil, olive oil, castor oil and sesame oil, glycerol fatty acid esters, polyethylene glycols and fatty acid esters of sorbitan or mixtures of these substances.

Suspensions, in addition to one or more compounds selected from biotin, the physiologically tolerable salts of biotin, biotin esters and the stereoisomeric forms of these compounds and one or more compounds selected from urea and urea derivatives, can contain the customary vehicles such as liquid diluents, e.g. water, ethanol or propylene glycol, suspending agents, e.g. ethoxylated isostearyl alcohols, polyoxyethylene sorbitan ester and polyoxyethylene sorbitan ester, microcrystalline cellulose, aluminum metahydroxide, bentonite, agar-agar and tragacanth or mixtures of these substances.

Soaps, in addition to one or more compounds selected from biotin, the physiologically tolerable salts of biotin, biotin esters and the stereoisomeric forms of these compounds and one or more compounds selected from urea and urea derivatives, can contain the customary vehicles such as alkali metal salts of fatty acids, salts of fatty acid monoesters, fatty acid protein hydrolyzates, isothionates, lanolin, fatty alcohol, vegetable oils, plant extracts, glycerol, sugar or mixtures of these substances.

Surfactant-containing cleansing products, in addition to one or more compounds selected from biotin, the physiologically tolerable salts of biotin, biotin esters and the stereoisomeric forms of these compounds and one or more compounds selected from urea and urea derivatives, can contain the customary vehicles such as salts of fatty alcohol sulfates, fatty alcohol ether sulfates, sulfosuccinic acid monoesters, fatty acid protein hydrolyzates, isothionates, imidazolinium derivatives, methyltaurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters or mixtures of these substances.

Face and body oils, in addition to one or more compounds selected from biotin, the physiologically tolerable salts of biotin, biotin esters and the stereoisomeric forms of these compounds and one or more compounds selected from urea and urea derivatives, can contain the customary vehicles such as synthetic oils such as fatty acid esters, fatty alcohols, silicone oils, natural oils such as vegetable oils and oily plant extracts, paraffin oils, lanolin oils or mixtures of these substances.

Preferably, the compounds selected from biotin, the physiologically tolerable salts of biotin, biotin esters and the stereoisomeric forms of these compounds, the penetration enhancers or promoters and/or the excipients are present in the galenic formulations according to the invention incorporated in colloidal carrier systems, in particular they are present incorporated in nanoparticles, liposomes or microemulsions.

Further typically galenic application forms are also lipsticks, lipcare sticks, mascara, eyeliner, eyeshadow, rouge, powder, emulsion and wax make-up, and sunscreen, pre-sun and after-sun preparations.

Preferred application forms are pastes, ointments, creams, emulsions, gels and lakes. In this context, the galenic formulation according to the invention is particularly preferably present as an O/W emulsion. The application to finger- and/or toenails is preferably carried out as a lake.

The proportion of the compound or of the compounds selected from biotin, the physiologically tolerable salts of biotin, biotin esters and the stereoisomeric forms of these compounds in the galenic formulation according to the invention is preferably from 0.05 to 5% by weight based on the total galenic formulation.

The proportion of the compound or of the compounds selected from urea and urea derivatives in the galenic formulation according to the invention is preferably from 1 to 40% by weight based on the total galenic formulation.

The galenic formulations, in addition to one or more compounds selected from biotin, the physiologically tolerable salts of biotin, biotin esters and the stereoisomeric forms of these compounds and one or more compounds selected from urea and urea derivatives, preferably contain one or more substances having free-radical scavenger properties, in particular vitamin E, vitamin C and/or their esters. The proportion of the compound or of the compounds having free-radical scavenger properties is preferably from 0.01 to 30% by weight, particularly preferably from 1 to 30% by weight, based on the total galenic formulation.

All compounds or components which can be used in the galenic formulations are either known and commercially obtainable or can be synthesized by known methods.

The following examples serve to illustrate the invention and are in no case to be interpreted as limiting. All percentages, if not stated otherwise, are percentages by weight.

The following compounds or components were used in examples 1 and 2:

| | |
|---|---|
| Biotin | Carl Roth GmbH, Karlsruhe, FRG |
| $^{14}$C-Biotin (spec. act. 55 mCi/mmol) | Amersham-Buchler GmbH, Brunswick, FRG |
| Chloroform, very pure p.a. | Merck KGaA, Darmstadt, FRG |
| Urea | Merck KGaA, Darmstadt, FRG |
| Carbon dioxide gas | Messer Griesheim, Leipzig, FRG |
| Lanette ®N | University Pharmacy of the Martin Luther University Halle Wittenberg |
| Methanol very pure p.a. | Laborchemie Apolda GmbH, FRG |
| Methanol gradient grade for HPLC | Merck KGaA, Darmstadt, FRG |
| Sodium chloride (NaCl), very pure p.a. | Merck KGaA, Darmstadt, FRG |
| Paraffinum subliquidum | Carl Roth GmbH, Karlsruhe, FRG |
| POPOP | Canberra Packard GmbH, Dreieich, FRG |
| PPO | Canberra Packard GmbH, Dreieich, FRG |
| Protein Assay Kit P5656 | Sigma-Aldrich Chemie GmbH, Deisenhofen, FRG |
| Serum free keratinocyte medium | (including Gibco BRL Life Technologies GmbH, Eggenstein, rEGF + BPE) FRG |
| Soluene 350 | Canberra Packard GmbH, Dreieich, FRG |
| Tesafilm | Beiersdorf AG, Hamburg, FRG |
| Toluene | Merck-Schuchardt, Hohenbrunn, FRG |
| Trimethylsulfonium hydroxide | Macherey Nagel GmbH, Düren, FRG |
| Vaselinum album | Carl Roth GmbH, Karlsruhe, FRG |

The INCI names of raw materials used are as follows:

| Raw material | INCI |
|---|---|
| Lanette ®N | Emulsifying cetylstearyl alcohol G.Ph. 10 |
| Paraffin | Mineral oil |
| Arlamol HD | Isohexadecane |
| Mirasil DM 350 | Dimethicone |
| Lanette ® O | Cetearyl alcohol |
| Span 60 | Sorbitan stearate |
| Montanov 68 | Cetearyl alcohol (and) cetearyl glucoside |
| Rhodicare S | Xanthan gum |
| Arlacel 165 V | Glyceryl stearate (and) PEG-100 stearate |
| Germaben II-E | Propylene glycol (and) diazolidinylurea (and) methylparaben (and) propylparaben |
| Isolan PDI | Diisostearoyl polyglyceryl-3 diisostearate |
| Cutina HR powder | Hydrogenated castor oil |

The following equipment and aids were used in the examples:

| | |
|---|---|
| Absorption reader | Labsystems, iEMS, Merlin, Bornheim-Hersel, FRG |
| Biopsy trephine | Stiefel Laboratorium GmbH, Offenbach, FRG |
| Liquid scintillation counter | Wallac 1410, Berthold, Berlin, FRG |
| Franz diffusion cell with waterbath | Crown Glass Company, Sommerville, New Jersey, USA Thermostat B3-DC1, Haake, Karlsruhe, FRG |
| GC unit | Finnigan MAT Magnum, GC-Varian 3400, Finnigan-MAT, Bremen, FRG |
| GC capillary column | FFAP, Macherey-Nagel, Düren or Fisher Scientific, Nidderau, FRG |
| Freezing microtome | Microtome Model 1206, Frigomobil Reichert-Jung, Heidelberg-Nussloch, FRG |
| Tissue culture flasks | Greiner GmbH, Frickenhausen, FRG |
| HaCaT keratiocytes | German Cancer Research Heidelberg, FRG |
| Precision balances | Type 870-13, Gottl. Kern & Sohn, Albstadt 1, FRG |
| Sterile filter, Nagene | Nalge-Company, Worcester, |

| -continued | |
|---|---|
| 0.2 μm | USA |
| Scintillation measuring vessels | Pony Vial, Pico Glass Vial, Econo Glass Vial, Canberra Packard GmbH, Dreieich, FRG |
| Vacuum rotary evaporator with waterbath | Rotivapor RE 111, Laboratoriums technik Büchli, Flawil, Switzerland Büchli 461, Laboratoriumstecknik Büchli, Flawil, Switzerland |

The buffer according to McIloaine used in Examples 1 and 2 corresponds to the buffer solution without biotin from examples 4 and 5 and is prepared as follows: 86 ml of 0.2 M disodium hydrogenphosphate monohydrate solution is mixed with 14 ml of 0.1 M citric acid monohydrate solution (pH: 7.2).

EXAMPLE 1

Investigations on the Lipid Content of Human Keratinocytes

Carrying out the Investigations on the Lipid Metabolism:

HaCaT cells (human adult low-calcium high-temperature keratinocytes) and native human keratinocytes are cultured in Gibco's keratinocyte serum-free medium (SFM) with addition of BPE (25 μg/ml bovine hypophysis extract) and rEGF (0.1–0.2 ng/ml, recombinant epidermal growth factor) in 5% strength $CO_2$ atmosphere (pH 7.2–7.4) at 36.6° C. in the low-calcium status (0.09 mM) in culture flasks (1 million cells/20 ml of SFM) and treated with the biotin solution (biotin dissolved in buffer according to McIloaine; medium concentration $10^{-7}$–$10^{-3}$ mol/l and solvent control) on the 3rd day after sowing. On the 6th day, the confluent monolayer is harvested and the samples are prepared, individual pellets up to 3 million cells each being used for the lipid extraction and for the protein determination.

Carrying out the Lipid Extraction:

The cells are extracted following the lipid extraction of Bligh and Dyer (B. E. Bligh et al. (1959) A rapid method of total lipid extraction and purification. Can. J. Biochem. Physiol. 37: 911–917). For this, the cell pellet is treated with 20 ml of a solvent mixture (chloroform: methanol=2:1), homogenized with stirring and extracted with shaking in the dark for 30 min. It is then filtered through a sterile filter and the extract is concentrated on a vacuum rotary evaporator.

The lipid film is taken up in 4 ml of methanol (gradient grade for HPLC) and analyzed via GC-MS.

Analysis of the Fatty Acids by Means of GC-MS:

The extracted lipids of the keratinocytes are analyzed as methanolic solutions via GC-MS in order to quantify the fatty acids contained therein. 100 μl of the solution are reacted with 1 μl each of 0.2 M trimethylsulfionium hydroxide to give methyl esters in order to improve the evaporability.

| Apparatus | Finnigan MAT Magnum, GC variant 3400 |
|---|---|
| Autosampler | Finnigan MAT A 200 S |
| Detector (MS) | Ion trap |
| Ionization | Electron impact 70 eV |
| Capillary column | FFAP, 25 m x 0.25 mm x 0.25 μm, with a 10 m uncoated precolumn |

| -continued | |
|---|---|
| Apparatus | Finnigan MAT Magnum, GC variant 3400 |
| Injection type | splitless, split valve opening after 1 min |
| Injection temperature | 250° C. |
| Temperature program | 60–160° C.: 15° C./min 160–240° C.: 25° C./min |
| Source temperature | 220° C. |
| Carrier gas | Helium, preliminary pressure 13 psi |
| Flow rate | 40 cm/min |
| Calibration | External standard (Concentrations: 0.02– 10 μg/ml) |

Determination of the Protein Content:

The protein content of the cells is determined according to the Lowry method using the protein assay kit. After preparation according to the procedure for the kit (P 5656), the measurement was carried out on an absorption reader at 690 nm.

The results of the influence of biotin on the fatty acid content of HaCaT keratinocytes are shown in FIGS. 1 to 4 for various concentrations of biotin (dissolved in buffer according to McIloaine). As control, the fatty acid content of the HaCaT keratinocytes after corresponding action of the buffer without biotin is moreover shown in FIGS. 1 to 4. The contents of the fatty acids myristic acid (MA), palmitic acid (PA), stearic acid (SA), oleic acid (OS) and linoleic acid (LA) are shown based on the protein content of the cells.

EXAMPLE 2

Penetration Investigations on Human Skin ex Vivo

Description of Model and Experimental Conditions:

To characterize the penetration behavior of biotin from different emulsions in excised human skin, FRANZ's diffusion cell is chosen as an in-vitro model. The selection of the model is based on the experience of the authors, who were able to detect correlating results between the in-vitro data of the model and the in-vivo results (R. J. Feldmann, et al. (1970): Absorption of some organic compounds through the skin in man. J. Invest. Dermatol. 54: 399–404: T. J. Franz (1975): Percutaneous absorption. On the relevance of in vitro data. J. Invest. Dermatol. 64: 190–195).

The basic unit of the FRANZ diffusion cell consists of a double-walled, temperature-controllable glass section. The acceptor liquid which is continuously kept in the homogeneous state by stirring is situated therein. In direct contact with the acceptor is the sample material on a gauze, which is stabilized by a glass ring and a metal clamp. A glass cover functions as evaporation protection for the upkeep of largely constant hydration conditions during the investigation period.

By means of the use of water as an acceptor medium, sink conditions for the hydrophilic active compound are realized in the single application of the vehicle to be investigated. For the standardization of the experimental conditions, use can be made of subject material having a low variation in age.

In order to obtain information about the extent of penetration of the active compound in the short-term and in the long-term range, recording of data is carried out after times of action of 30 and 300 min.

An O/W emulsion according to the invention (water-containing hydrophilic ointment) comprising biotin and urea is prepared from the following components:

|   |                                                                       |     | % by weight |
|---|-----------------------------------------------------------------------|-----|-------------|
| B | Lanette N                                                             | (1) | 9.0         |
|   | Paraffinum subliquidum                                                | (2) | 10.5        |
|   | Vaselinum album                                                       | (2) | 10.5        |
| A | Water, demineralized and buffer according to McIloaine (weight ratio = 50:50) |   | to 100    |
|   | Biotin                                                                | (2) | 0.1         |
|   | Urea                                                                  | (3) | 10.0        |

Preparation:

The active compound biotin is first dissolved in the buffer according to McIloaine and dispersed in demineralized water together with the urea (applicable only in the case of the urea-containing formulation according to the invention). The proportionate incorporation of the water phase B into the molten lipophilic phase A of the residual constituents of the emulsion then takes place. The system is stirred until it has cooled.

Reference Sources:

(1) University Pharmacy of the Martin Luther University Halle-Wittenberg (2) Carl Roth GmbH, Karlsruhe (3) Merck KGaA, Darmstadt Preparation of the Biological Material:

The skin preparations used for the penetration studies are derived from breast reduction plastic surgery. The investigation material is worked up within 2h–4h after the operation. For this, cleaning with isotonic NaCl solution is carried out first. The mechanical removal of the subcutaneous fatty tissue and the preparation of round pieces with the aid of a punch (d=2 cm) follows, so that afterward preparations packed individually in aluminum foil can be stored at −20° C. in a deep-freeze for a maximum of three months.

The age of the subjects was between 17 and 53 years, it being attempted for reasons of standardization in the experimental planning to make use largely of skin of the same age.

Experiments with Radiolabeled Substances:

About 30 min. before the start of the experiment, the FRANZ diffusion cells are filled with the acceptor medium water and adjusted to a temperature of 32° C. Immediately before the application of vehicle, this is treated with the tracer $^{14}$C-biotin (5 $\mu$Ci) dissolved in ethanol. Homogeneous mixing with the unlabeled preparation and the complete evaporation of the solvent is to be considered important here. The homogeneous application of about 20 mg of emulsion to the entire epidermal surface of a piece of skin which has been thawed and dried of freezing water with a cotton bud then takes place. Immediately after the application of vehicle, this piece of skin is placed on a gauze and fixed in the diffusion cell.

After the passage of experimental times of 30 min. and 300 min., the skin is removed from the model and the formulation residue is carefully removed with cotton buds. Further work-up requires the fixing of the investigation material with pins on the periphery to a polystyrene substrate covered with aluminum foil. With the aid of a template, the horny layer can be completely eliminated reproducibly on a circular area (d=1.6 cm) by detachment of Tesafilm 20 times. It is determined quantitatively in fractionation of the detachments in pairs (10×2). Three punch biopsies each (d=0.6 cm) which serve for the preparation of horizontal sections (8×20 $\mu$m—epidermis, 30×40 $\mu$m—dermis) on a freezing microtome are removed from the living skin. For the quantification of the samples, these are treated with methanol and scintillator [4.0 g of PPO (2,5-diphenyloxazole) and 0.1 g of POPOP 1,4-di-2-(5-phenyloxazolyl)benzene in 1.0 l of toluene)], the epidermal and dermal sections and the punch residues having been left overnight beforehand in 100 $\mu$l or 1 ml of Soluene in the scintillation measuring vessel for the complete disintegration of the tissue. Following this, the samples are measured in the liquid scintillation counter with addition of two blank values.

Figure 1:
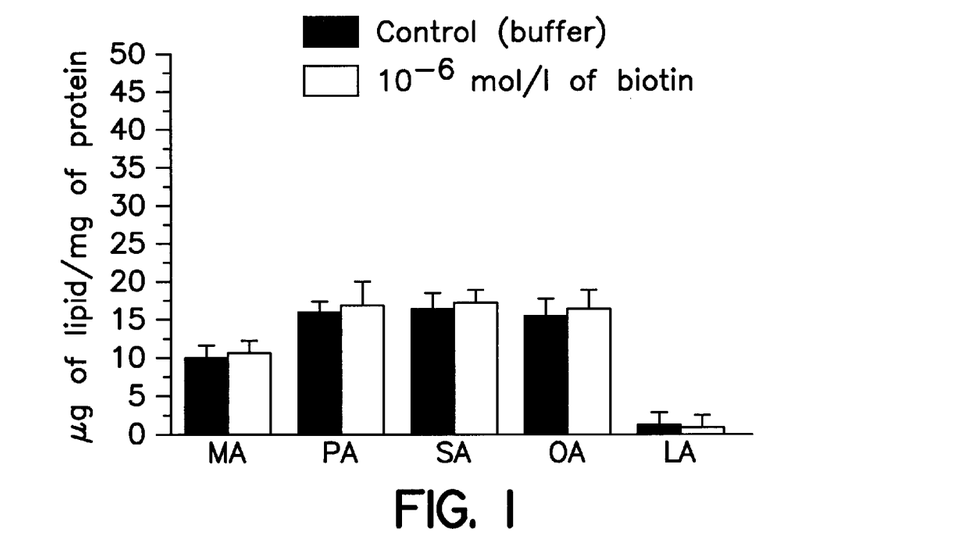
Figure 2:
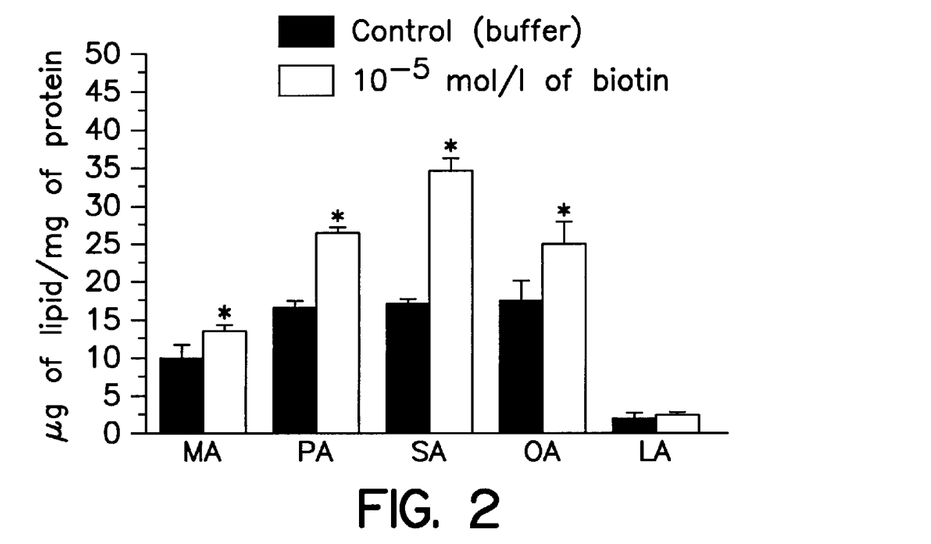
Figure 3:
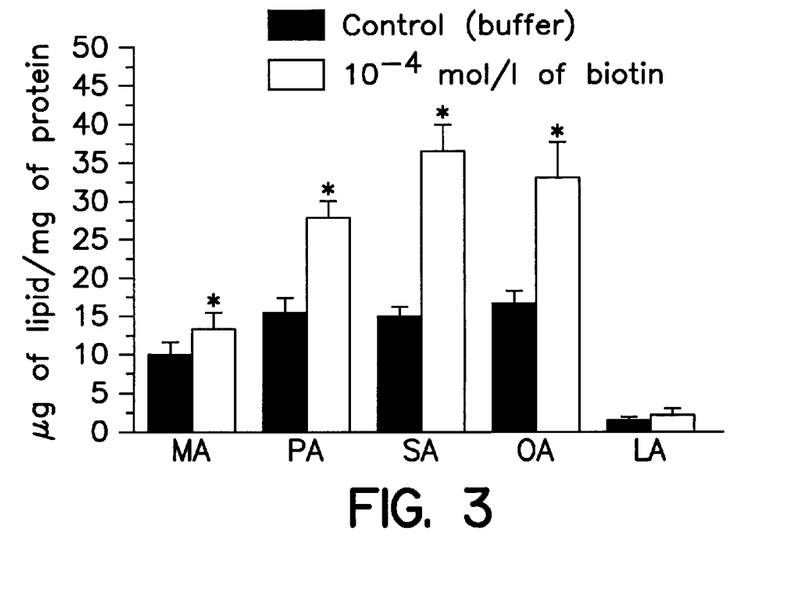
Figure 4:
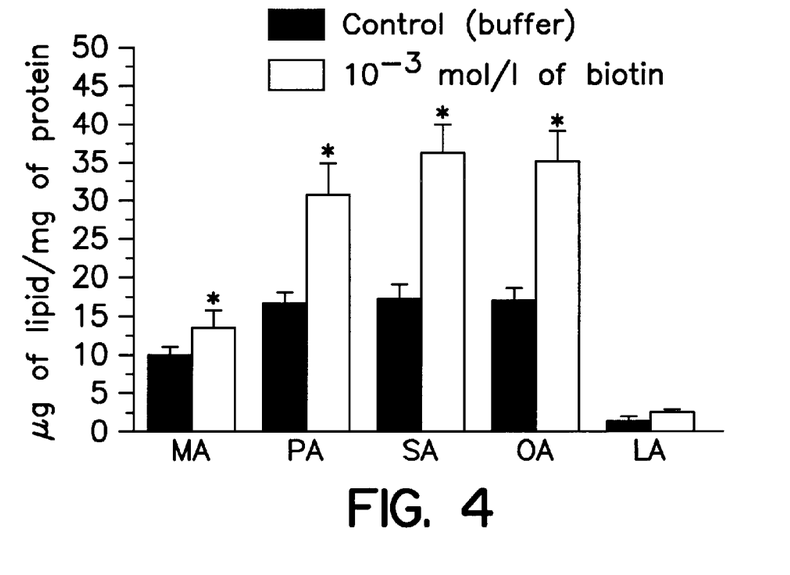
Figure 5:
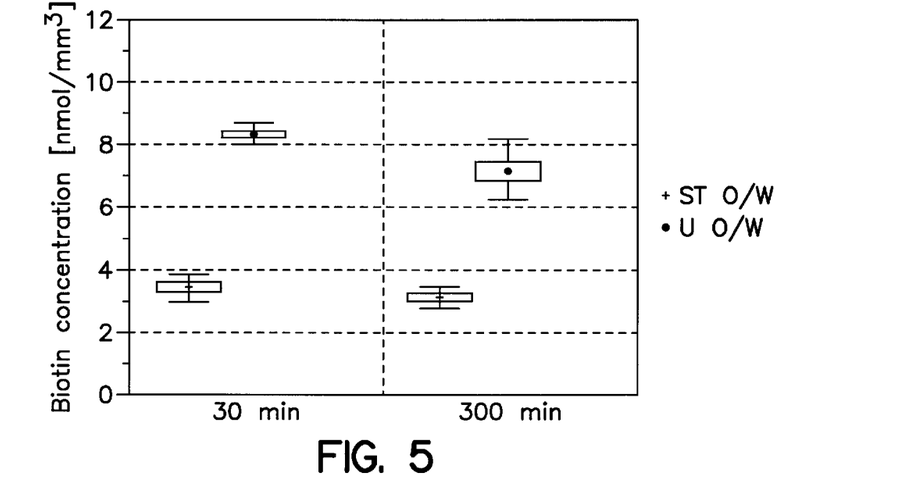
Figure 6:
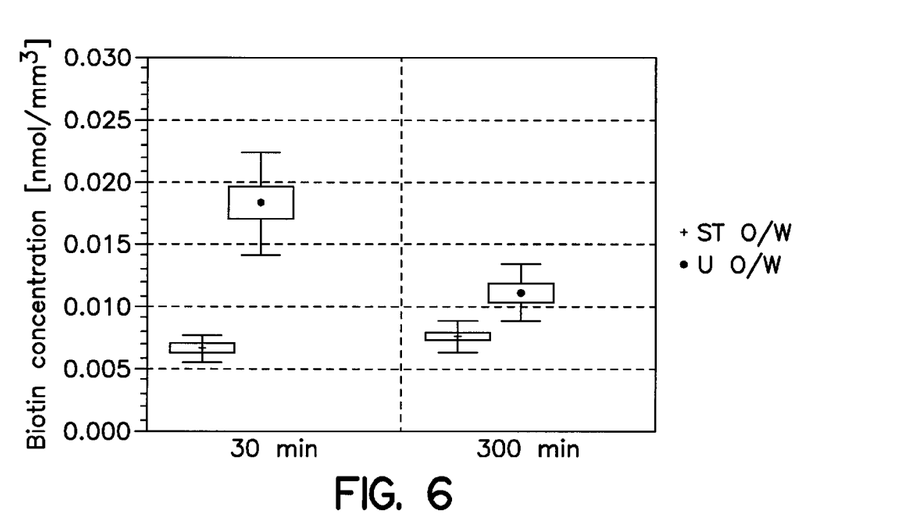

The results for the penetration of biotin from the O/W ointment according to the invention of this example comprising 10% by weight of urea (see values for U O/W) are shown for times of action of 30 min. and 300 min. in FIG. 5 for the horny layer, in FIG. 6 for the epidermis and FIG. 7 for the dermis. As a comparison, in FIGS. 5 to 7 the results are moreover shown for the penetration of biotin from an ointment prepared corresponding to the O/W ointment according to the invention, but in which urea is replaced by a solution consisting of 50% by weight of demineralized water and 50% by weight of buffer according to McIloaine (see values for ST O/W). The results are shown as the concentration (nmol of biotin per mm3 of horny layer, epidermis or dermis).

EXAMPLE 3

A hand and nail cream according to the invention comprising biotin and urea is prepared from the following components:

|   |                                       |     | % by weight |
|---|---------------------------------------|-----|-------------|
| A | Paraffin (Item No. 107162)            | (1) | 2.0         |
|   | Arlamol HD                            | (2) | 2.0         |
|   | Isopropyl palmitate                   | (3) | 3.0         |
|   | Soya Oil                              | (4) | 0.5         |
|   | Mirasil DM 350                        | (5) | 1.0         |
|   | Lanette O                             | (3) | 1.0         |
|   | Span 60                               | (2) | 1.5         |
|   | Montanov 68                           | (6) | 4.0         |
|   | (−)-α-Bisabolol (Item No. 130170)     | (1) | 0.3         |
| B | Water, demineralized                  |     | to 100      |
|   | Glycerol, 87% strength (Item No. 104091) | (1) | 10.0     |
|   | D-Panthenol                           | (7) | 0.5         |
|   | D-(+)-Biotin (Item No. 130220)        | (1) | 0.05        |
|   | Urea                                  | (1) | 10.0        |
|   | Preservative                          |     | q.s.        |
| C | Rhodicare                             | (5) | 0.3         |
| D | Perfume Bianca                        | (8) | 0.2         |

The preservatives used can be 0.05% propyl 4-hydroxybenzoate (Item No. 107427), 0.15% methyl 4-hydroxybenzoate (Item No. 106757) or 0.30% Germall 115 (ISP, Frechen).

Preparation:

The combined phases A and B are separately heated to 75° C. Phase C is then slowly added to phase B with stirring at 75° C. and stirred until a homogeneous mixture results. Phase A is then added and the mixture is stirred until it is homogeneous. It is allowed to cool with stirring and the perfume is added at about 35° C.

Suppliers:

(1) Merck KGaA, Darmstadt (2) ICI Surfactants, Essen (3) Henkel KGaA, Düsseldorf (4) Gustav Heess, Stuttgart (5) Rhodia, Frankfurt
(6) Seppic, France
(7) BASF AG, Ludwigshafen
(8) H&R, Holzminden

EXAMPLE 4

An O/W emulsion according to the invention comprising biotin and urea is prepared from the following components:

|   |                              |     | % by weight |
|---|------------------------------|-----|-------------|
| A | Paraffin, viscous            | (1) | 8.0         |
|   | Isopropyl myristate          | (1) | 7.0         |
|   | Lanette O                    | (2) | 3.0         |
|   | Arlacel 165 V                | (3) | 5.0         |
| B | Water, demineralized         |     | to 100      |
|   | Glycerol, 87% strength       | (1) | 3.0         |
|   | Urea                         | (1) | 10.0        |
|   | Biotin buffer solution (1% strength) | (1) | 10.0 |
|   | Germaben II-E                | (4) | 0.5         |

Preparation:

The combined phases A and B are separately heated to 75° C. Phase A is slowly added to phase B with stirring and the resulting emulsion is homogenized. It is then allowed to cool to 30° C. with stirring.

Suppliers:

(1) Merck KGaA, Darmstadt
(2) Henkel KGaA, Düsseldorf
(3) ICI
(4) ISP

EXAMPLE 5

A W/O emulsion according to the invention comprising biotin and urea is prepared from the following components:

|   |                              |     | % by weight |
|---|------------------------------|-----|-------------|
| A | Isolan PDI                   | (2) | 3.0         |
|   | Paraffin oil, liquid         | (1) | 17.0        |
|   | Isopropyl myristate          | (1) | 5.0         |
|   | Wax, bleached                | (1) | 0.2         |
|   | Cutina HR powder             | (3) | 0.3         |
| B | Water, demineralized         |     | to 100      |
|   | Glycerol, 87% strength       | (1) | 4.0         |
|   | Urea                         | (1) | 10.0        |
|   | Biotin buffer solution (1% strength) | (1) | 10.0 |
|   | Magnesium sulfate heptahydrate | (1) | 0.5       |
|   | Germaben II-E                | (4) | 0.5         |

Preparation:

The combined phases A and B are separately heated to 75° C. Phase B is then slowly added to Phase A with stirring and homogenized. The mixture is then allowed to cool to room temperature with stirring.

Suppliers:

(1) Merck KGaA, Darmstadt
(2) Th. Goldschmidt
(3) Henkel KGaA, Düsseldorf
(4) ISP

What is claimed is:

1. A galenic formulation comprising:
   (a) at least one compound selected from the group consisting of biotin, a physiologically tolerable salt of biotin, a biotin ester, and the stereoisomeric forms of these compounds, and
   (b) urea or a urea derivative, wherein the proportion of the urea or the urea derivative is from 1 to 40% by weight based on the total galenic formulation.

2. The galenic formulation according to claim 1, wherein the proportion of the compound or of the compounds selected from the group consisting of biotin, a physiologically tolerable salt of biotin, a biotin ester and the stereoisomeric forms of these compounds is from 0.05 to 5% by weight based on the total galenic formulation.

3. The galenic formulation according to claim 1, wherein said formulation contains-biotin.

4. The galenic formulation according to claim 1, wherein said formulation contains urea.

5. The galenic formulation according to claim 1, wherein said formulation contains at least one substance having free-radical scavenger properties.

6. The galenic formulation according to claim 1, wherein said formulation is present in the form of a solution, a suspension, an emulsion, a paste, an ointment, a gel, a cream, a lotion, a lake, a powder, a soap, a surfactant-containing cleansing preparation, an oil, a lipstick, a lipcare stick, mascara, an eyeliner, eye shadow, rouge, a powder, an emulsion, wax make-up, a sunscreen, pre-sun and after-sun preparation or a spray.

7. A method for preparing a topically applicable galenic formulation comprising formulating
   (a) at least one compound selected from the group consisting of biotin, a physiologically tolerable salt of biotin, a biotin ester, and the stereoisomeric forms of these compounds, and
   (b) urea or a urea derivative, wherein the proportion of the urea or urea derivative is from 1 to 40% by weight based on the total galenic formulation.

8. A method for treating diseases or functional disorders of human or animal skin, hair or nails comprising administering an effective amount of a topically applicable galenic formulation prepared according to claim 7.

9. The method of claim 8 the therapy, prophylaxis or metaphylaxis of skin diseases or functional disorders of the skin, for skin aging processes or for treating dry skin conditions.

10. A method for improving the penetration of a biotin compound into deeper layers of human or animal skin, mucous membrane or nails, comprising applying an effective amount of the topically applicable galenic formulation prepared according to claim 7.

11. A method for the protection, or maintenance or reconstruction of the normal function and structure of human or animal skin or for the prevention of environmentally related skin damage comprising applying an effective amount of the topically applicable galenic formulation prepared according to claim 7.

12. A method for the treatment of diseases of the hair, sebaceous or sweat glands of human or animal skin comprising applying an effective amount of the topically applicable galenic formulation prepared according to claim 7.

13. A method for cosmetic skin treatment comprising applying an effective amount of the topically applicable galenic formulation prepared according to claim 7.

14. The process for preparing a topically applicable galenic formulation characterized in that according to claim 7, further comprising active compounds, excipients and or vehicles.

15. A galenic formulation comprising:
(a) at least one compound selected from the group consisting of biotin, a physiologically tolerable salt of biotin, a biotin ester, and the stereoisomeric forms of these compounds, and
(b) urea or a compound which releases urea after cleavage, wherein the proportion of the urea or the compound which releases urea after cleavage is from 1 to 40% by weight based on the total galenic formulation.

16. The galenic formulation according to claim 1, wherein said urea derivative is allantoin.

* * * * *

UNITED STATES PATENT AND TRADEMARK OFFICE
CERTIFICATE OF CORRECTION

PATENT NO. : 6,660,251 B1
DATED : December 9, 2003
INVENTOR(S) : Bünger et al.

It is certified that error appears in the above-identified patent and that said Letters Patent is hereby corrected as shown below:

Column 14,
Line 8, delete "from 1 to 40 %" and add -- at least 1 % --
Line 14, delete "from 0.05 to 5 %" and add -- at least 0.05 % --
Line 37, delete "from 1 to 40 %" and add -- at least 1 % --

Column 16,
Lines 1-2, delete "from 1 to 40 %" and add -- at least 1 % --

Signed and Sealed this

Thirteenth Day of April, 2004

JON W. DUDAS
*Acting Director of the United States Patent and Trademark Office*